Figure 1:
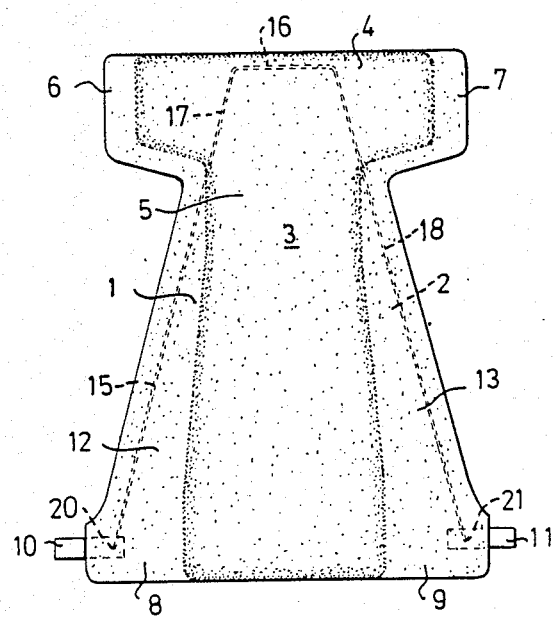

United States Patent [19]

Widlund et al.

[11] Patent Number: 4,692,163
[45] Date of Patent: Sep. 8, 1987

[54] ABSORPTION ARTICLE SUCH AS A DIAPER OR A SANITARY NAPKIN, AND A METHOD FOR THE MANUFACTURE THEREOF

[75] Inventors: Leif U. R. Widlund; Maj I. Ternstrom, both of Mölnlycke, Sweden

[73] Assignee: Molnlycke AB, Gothenburg, Sweden

[21] Appl. No.: 802,216

[22] Filed: Nov. 26, 1985

[30] Foreign Application Priority Data

Nov. 30, 1984 [SE] Sweden .............................. 8406071

[51] Int. Cl.⁴ ............................................. A61F 13/16
[52] U.S. Cl. ................................................. 604/385 A
[58] Field of Search ................ 604/385.1, 385.2, 366, 604/367, 370, 371, 394; 156/164

[56] References Cited

U.S. PATENT DOCUMENTS 3,860,003  1/1975  Buell .
4,050,462  9/1977  Woon et al. .
4,319,572  3/1982  Widlund et al. ..................... 604/389
4,407,284 10/1983  Pieniak ............................ 604/385.2
4,425,127  1/1984  Suzuki et al. ..................... 604/385.2
4,515,595  5/1985  Kievit et al. ..................... 604/385.2

FOREIGN PATENT DOCUMENTS 218632   12/1957  Australia .
2063794   7/1971  France .
7201114-1  3/1975  Sweden .
82020900   4/1982  Sweden .
7905765-9 11/1982  Sweden .

Primary Examiner—John D. Yasko
Attorney, Agent, or Firm—Young & Thompson

[57] ABSTRACT

The invention relates to absorption articles such as diapers or sanitary napkins comprising partly a liquid permeable first outer layer and a preferably liquid impermeable second outer layer applied to either side of an absorption body encased therein; partly elastic members applied under tension and intended for bringing the edge portions of said article into tightly sealing contact with the body of the wearer. The primary distinguishing feature of the inventive article is that the elastic members are comprised in a network.

24 Claims, 18 Drawing Figures

ABSORPTION ARTICLE SUCH AS A DIAPER OR A SANITARY NAPKIN, AND A METHOD FOR THE MANUFACTURE THEREOF

The present invention relates primarily to to an absorption article such as a diaper or a sanitary napkin, comprising a liquid permeable first outer layer and a preferably liquid impermeable second outer layer applied to either side of an absorption body for the accommodation thereof, and elastic members applied under tension and serving to bring the edge portions of said article into sealing contact with the body of the wearer. Secondly, the invention relates to a method of producing such absortion articles.

A problem associated with conventional disposable diapers is that their absorption body has a certain stiffness making it difficult, when securing the diapers by means of adhesive tape, to impart the desired close fit to the body of the wearer. Due to the stiffness of the absorption body it cannot be avoided, especially after having used the diaper a certain period of time, that a gap is formed between the diaper and the baby's waist and/or between the diaper and the baby's legs, which may result in leakage.

In attempts to eliminate the risk of leakage, there has been suggested the possibility of supplementing so-called complete disposable diapers with elastic ribbons or the like which would provide for the diaper to be tightly sealed around the wearer. As a result of this, there is available on the market various types of disposable diapers having elastic ribbons or threads extending along their side edges. The common factor of these known types of disposable diapers comprising elastic ribbons or threads is that the ribbons or threads have been applied for the primary purpose of preventing the leakage of urine.

U.S. patent application Ser. No. 3,860,003, for example, teaches a diaper the crotch region of which is provided with flexible side flaps extending out from and along the side edges of the absorption body. The width of the absorption body is considerably less in the crotch portion than over the remaining part of the diaper, and an elastic ribbon is attached to either side flap at a distance of at least 19 mm from the side edge of the absorption body. In this way elastic side flaps will be obtained providing a close fit of the diaper to the legs of the baby.

The arrangement of the elastic flaps does in fact seem to reduce the risk of urine leakage but still involves certain drawbacks. For example, liquid from the absorption body is collected inside the elastic flaps giving rise to skin irritation. Furthermore, the width of the absorption body in the crotch area must be substantially reduced in order for the elastic flaps to be sufficiently wide, which results in that the absorbing material becomes very wet when using the diaper, thereby giving rise to urine leakage despite the presence of the sealing elastic ribbons. The heavily reduced dimension in the crotch area of the absorption body will also cause the absorption body to disintegrate around the crotch due to the large amount of liquid present in this region, preventing in this manner the transmission of liquid to unused portions of the absorption body.

These disadvantages, associated with a diaper performed in accordance with U.S. patent application Ser. No. 3,860,003, are defined more closely in U.S. patent application Ser. No. 4,050,462 according to which another design of diaper has been chosen in order to eliminate said drawbacks. In a diaper manufactured in accordance with the latter publication, the elastic ribbons as well are affixed to the crotch area of the diaper but as close to the absorption body as is practically feasible. In this manner the absorption body in the croth area will be contracted by the elastic ribbons, the volume of the absorption body in the crotch area thereby increasing. The combination of increased absorption capacity per surface unit in the crotch area and the sealing action of the ribbons around the legs of the wearer, according to the latter publication, would result in that the risk of urine leakage is almost totally eliminated. It is also implied in said publication that the irregularities created in the crotch area of the absorption body would serve as cushions counteracting chafing caused by the elastic ribbons and leaving marks on the child's skin. Even though these cushions, contrary to expectation, would contribute to somewhat mitigate the tendency of the elastic ribbons to chafe the skin, it cannot be avoided that elastic ribbons in the crotch area and alongside the absorption body will give rise to significant chafing of the child's legs. When the child moves by crawling or walking, the movements of the legs will cause a highly increased tension in the elastic ribbons which could result in chafe marks around the child's legs.

In the two above-mentioned prior art diapers provided with elastic ribbons, threads or the like, the ribbons are not either attached so as to allow for the diaper to adapt to the bodily shape of the child, because there have been used two elastic ribbons or the like extending substantially parallel along the length of the diaper.

In relation to the two diapers described above, the Swedish patent specification SE-B No. 7905765-9 relates to a considerably improved diaper construction with regard to fitness, since the elasticity in this diaper is better adapted to the bodily shape of an infant, and therefore it will fit more closely around the body of the wearer thereby improving the safety against leakage.

A diaper performed in accordance with the latter publication is so designed that its outer layer extends laterally outside the edges of the absorption body with a continuously increasing distance from said edges in the direction towards the rear end of the diaper, starting from the crotch portion, thereby forming flaps with gradually increasing width on either side of the absorption body. The elastic is applied in a principally V-shaped pattern, the apex of the pattern being located at the center of the diaper front end and the portions of the pattern projecting from the apex extending from the center of the diaper front end to the end of the crotch portion, and further along the edges of the flaps to the rear end of the diaper, enabling in this way the flaps of the diaper during use to be closely fit to the buttocks of an infant.

In fact, the elastic in the last-mentioned diaper construction functions quite well although not optimally, however. The elastic ribbons or threads therein extend in straight paths, but with regard to the bodily shape of an infant, these paths should rather be curved for improving the bodily adaption. In comparison with conventional pants having curved elastic around the leg openings for adapting to the human body, it is easily understood that the elastic in diapers should be arched.

The highest degree of security against diaper leakage available so far has been attained with diapers held in place on the baby's body by means of elastic pants specifically designed for this purpose. A substantial drawback in this connection however is the requirement of two separate parts; the diaper and the pant, which makes attachment complicated. Despite the fact that a diaper applied by means of the pant provides a close fit to the baby's body, leakage may still occur, especially through the side edges of the absorption body.

FR-A 2,063,794 does teach disposable diapers having rounded elastic around the wearer's legs, i.e. the elastic is affixed in the same way as in a pant, but to achieve the rounded elastics however it has to be stiched on, which for economic reasons is completely inconceivable with regard to a modern diaper made for one-time use.

There has also been suggested the use of elastic on menstrual articles such as sanitary napkins and panty protectors. SE-B-8202090-0 for example teaches sanitary napkins and panty protectors having longitudinal edge elastic which is attached to edge portions projecting from both sides of the absorption body and serves to elevate the respective edge portion for providing a border around the absorption body. Although this arrangement improves the protection against side leakage, many problems still remain unsolved. Sanitary napkins and panty protectors are in fact usually planar and more or less rectangular, resulting in poor adaptation to the bodily shape of the wearer while being deformed in an almost totally uncontrollable manner during use. Such deformation or warping of the article may even cause the menstrual fluid to leak out instead of being appropriately collected therein.

The shortcomings of prior art diapers, sanitary napkins and panty protectors discussed above have however been entirely overcome with the present invention, primarily because the elastic members included in the inventive absorption article are part of a netting which may also comprise inelastic members. By arranging the elastic in the form of a network, individual ribbons or threads therein can be deflected by means of crossing threads, obtaining in this manner elasticity curvatures suitable for an absorption article. With the use of an elastic network according to the invention, even initially planar absorption articles can be given a three-dimensional shape well adapted to the body of the wearer.

A plurality of embodiments of networks performed in accordance with the invention and including elastic used for various types of absorption articles are set forth in the claims.

As already mentioned, the invention also relates to a method of manufacturing absorption articles such as sanitary napkins and diapers. More closely, the inventive method relates to the application of elastic members in continuous manufacture of an absorption article such as a diaper or a sanitary napkin, whereby individual absorption cores are fed out on a production line to be enclosed between a web of liquid permeable material, preferably a non-woven textile material, and a web of liquid impermeable material, preferably a plastic film, said webs of material being united around each absorption core and then cut in between for producing single absorption articles.

The novel and primarily distinguishing feature of the inventive method is that a network comprising elastic members is advanced while keeping pace with the webs of material and is affixed to at least one web, or to an additional web of material which may be simultaneously fed and which is joined to the exterior of the liquid impermeable web of material, said network then being cut off together with the webs of material to form separate absorption articles provided with elastic. A plurality of various embodiments of this novel method for the application of networks, serving as elastic members in absorption articles of the kind in question, are also set forth in the claims.

With the use of elastic members in the form of nettings according to the present invention, so-called longitudinal and transverse elastic can be combined for example to form diapers and sanitary napkins, and to achieve sealing elastic.

Figure 2:
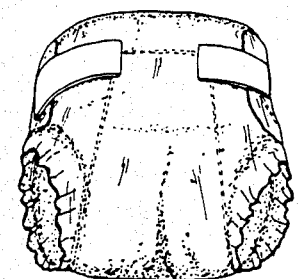
Figure 3:
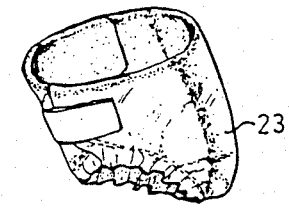
Figure 4:
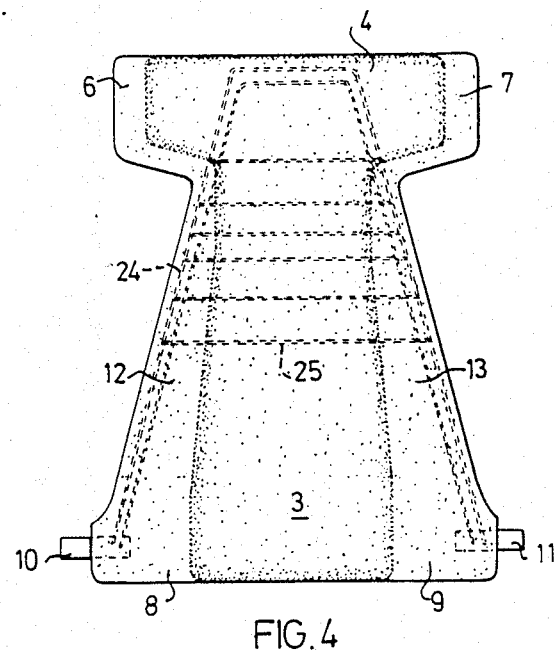
Figure 5:
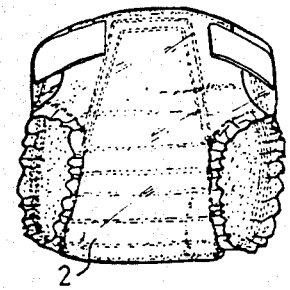
Figure 6:
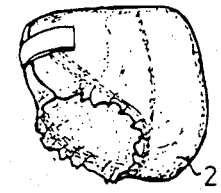
Figure 7:
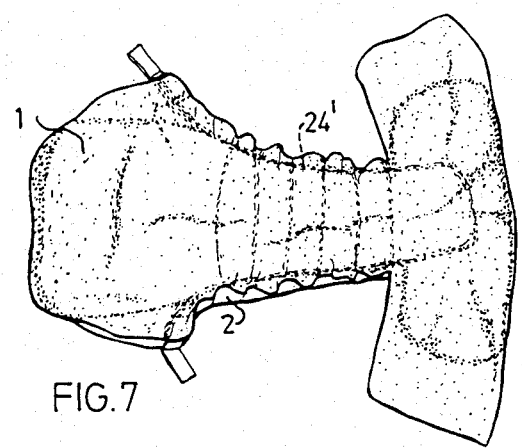
Figure 8:
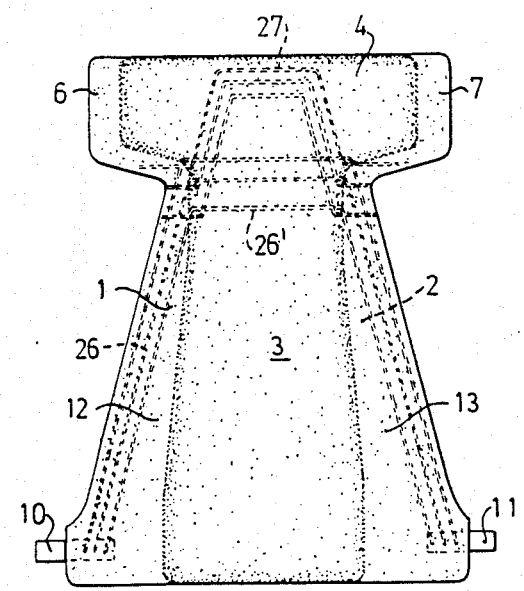
Figure 9:
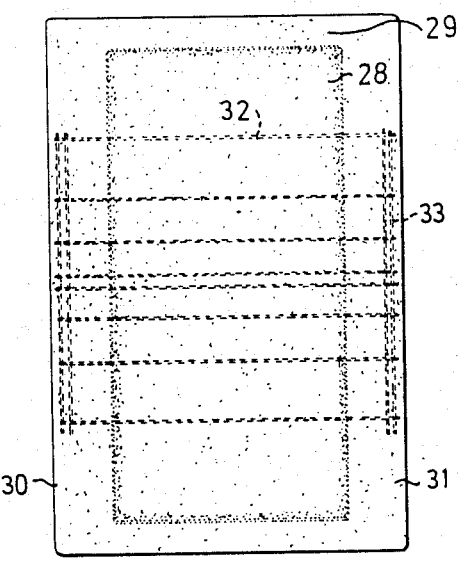
Figure 10:
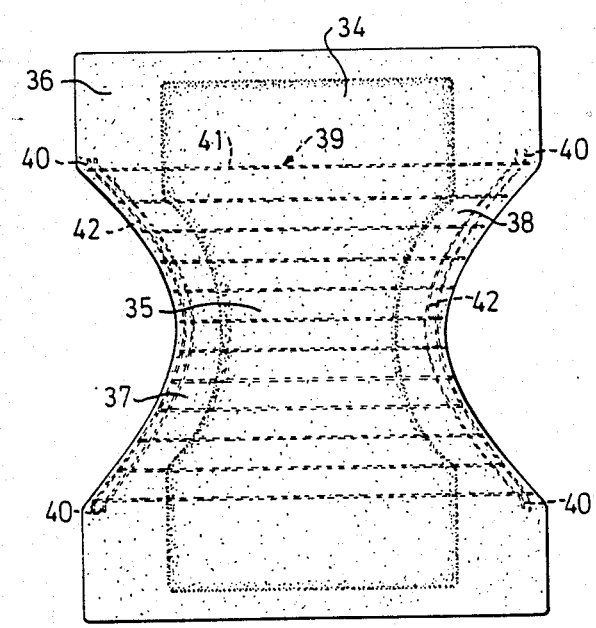
Figure 11:
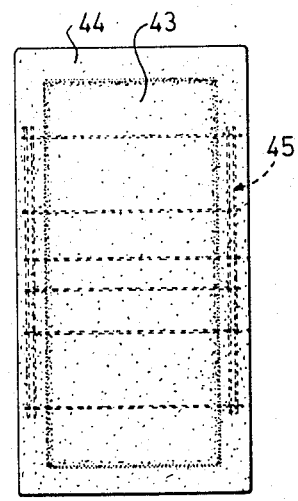
Figure 12:
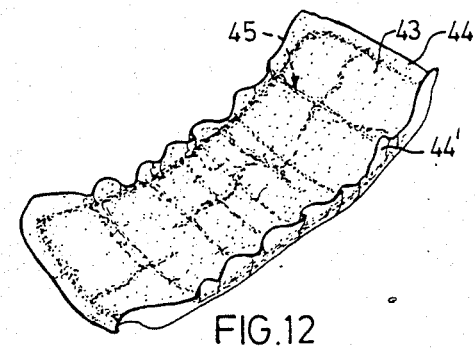
Figure 13:
Figure 14:
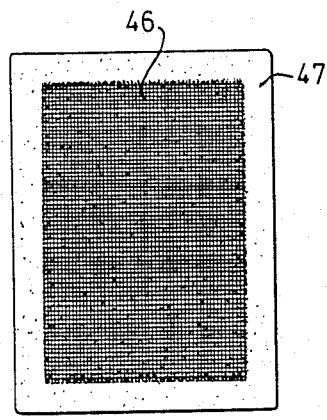
Figure 15:
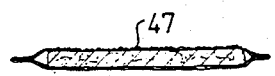
Figure 16:
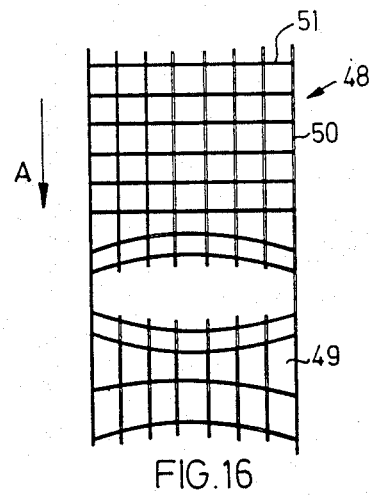

The invention will be described in more detail below while referring to a number of embodiments illustrated in the accompanying drawings, wherein FIG. 1 of the drawings shows a prior art diaper provided with sealing elastic, FIGS. 2 and 3 show the diaper when put on and seen from the front and from the side, FIG. 4 is a view of an embodiment of a diaper made according to the invention and shown in a stretched condition, the appearance reminiscing the prior art diaper of FIG. 3 but being provided with the elastic stipulated according to the invention, FIGS. 5 and 6 show this diaper when put on and seen from the front and from the side, FIG. 7 shows the diaper of FIGS. 4–6 in a non-stretched condition, FIG. 8 shows a somewhat modified diaper as compared to that of FIG. 4, FIGS. 9 and 10 show two additional embodiments of the diaper in a stretched state and made according to the invention with network elastic, FIGS. 11–13 show a sanitary napkin made according to the invention and provided with elastic, FIG. 14 is a view of an absorption article in a stretched state, made according to the invention and provided with network elastic, FIG. 15 is a cross section through the article of FIG. 14, whereas FIG. 16 illustrates a method of producing a network elastic incorporated in an absorption article made according to the invention, FIGS. 17 and 18 finally showing two further embodiments of this inventive method.

The prior art diaper illustrated in FIGS. 1–3 consists of a first outer layer 1 of a liquid permeable, preferably non-woven textile material intended to face the wearer's body during use, a second outer layer 2 of a liquid impermeable material such as polyethene for example, and an absorption body 3 disposed between the two outer layers 1,2.

At one end, the absorption body has a transverse portion 4 as shown in FIG. 1 for broadening the width of this end, and being intended for application in front of the child's legs during use. Furthermore, the absorption body is made thicker within an area 5 at the crotch portion of the diaper, i.e. substantially behind the widened transverse portion. The two outer layers 1, 2 extending laterally outside the absorption body are formed as attachment flaps 6, 7 and 8, 9 at either end of the diaper and are intended for application around the waist of the infant. Adhesive strips 10, 11 are affixed onto both rear flaps 8, 9 of the diaper, by means of which the flaps at the front and rear ends of the diaper can be united when putting the diaper on the child. Starting from a point at the crotch portion of the diaper, the outer layers 1, 2 extend with a continuously increasing distance laterally outwards from the two side edges of the absorption body, creating in this way substantially triangular flaps 12, 13 on either side of the absorption body.

The two outer layers 1,2 are joined together along their edge portions and are also united, as well as connected with the absorption body 3, by means of transverse beads of binding agent.

An elastic thread or the like 15 is applied in a generally V-shaped pattern over this prior art diaper. The apex 16 of said V-shaped pattern is situated at the center of the diaper front end, from which thread portions 17, 18 extend along a substantially straight line over the absorption body and from there to the diaper rear end along the outer edge portion of each triangular side flap. The elastic thread or the like 15 is applied between the two outer layers 1, 2 and is secured thereto at the apex 16 of the thread pattern as well as at the two thread end portions 20, 21. At several spaced points along its extension, the eleastic thread 15 is further connected by means of the transverse binder beads to the outer layers 1, 2 and the absorption body 3.

The prior art elastic illustrated in FIG. 1 has several advantages over straight, parallel, elastic threads by the V-shaped elastic affording a good fit to the diaper and a close sealing contact to the outside of the wearer's thighs; see FIG. 3. As shown in FIGS. 1 and 2, the fit of the diaper is however not altogether perfect.

Despite the relatively narrow dimension of the diaper in the crotch portion thereof, there is the risk that this portion becomes somewhat deformed during use; see for example the indentation denoted 22 in FIG. 2, which may lead to additional deformations and possibly leakage. As shown in FIG. 3, the absorption body also bulges heavily at the baby's back as denoted by 23, thereby making the diaper rather uncomfortable to wear.

The embodiment shown in FIG. 4 of a diaper made in accordance with the invention corresponds on the whole to the diaper of FIG. 1, except with regard to elastic. The components corresponding to similar details in FIG. 1 have therefore been given the same reference numerals in FIG. 4.

A diaper according to the embodiment of FIG. 4 is provided with a network elastic according to the invention, said elastic consisting of longitudinal as well as transverse elastic ribbons or threads 24, 25 which, according to the embodiment of FIG. 4, are applied to the liquid permeable layer 1, the elastic netting created by said threads or ribbons forming the absorption body both transversely and longitudinally. As shown in FIG. 4, the transverse elastic threads are applied while being most closely spaced in the crotch portion, which means that the absorption core has its minimum width in that zone. The elastic tension around the absorption body in this inventive diaper will counteract unintentional cavities such as the indentation denoted 22 in FIG. 2.

With a network elastic according to the embodiment shown in FIGS. 4-7 and relating to the inventive absorption article, the liquid permeable outer layer 2 will form a basin-like space accommodating the absorption body, the longitudinal threads or ribbons in the elastic netting simultaneously forming an edge elastic; see particularly FIG. 5.

The netting elastic in an absorption article made according to the invention further makes the absorption body included therein more stable and shape permanent, in contrast to the prior art diapers having absorption bodies made of cellulose fluff pulp involving instead the problem of the fluff pulp tending to slide in relation to the surrounding casing. In numerous prior art diapers this has caused the formation of gaps in the absorption body occurring most frequently in the narrow crotch portion.

By employing the net elastic shown in FIGS. 4-7, the liquid impermeable layer is applied with no further arrangements around the side edges of the absorption body, and the edge elastic of the netting is situated during use of the diaper right in front of, or even within the side edges of the absorption body; see FIG. 5. In this way the elastic will afford excellent protection against leakage.

When comparing the diapers shown in FIGS. 3 and 6, it is clearly seen that the inventive diaper shown in FIG. 6 provides better fitness while being less space-consuming than the prior art diaper of FIG. 3. Furthermore, the large bulge at 23 on the diaper shown in FIG. 3 is almost completely eliminated on the inventive diaper shown in FIG. 6.

Another essential advantage associated with the inventive net elastic is the possibility of giving single elastic threads in the netting the desired curvature.

In the embodiment shown in FIGS. 4-7, the transverse elastic threads are more closely spaced at the crotch portion than over the rest of the diaper. As shown in FIG. 7, this results in the edge elastics 24' being rounded. The curvature of the edge elastic can thus be optimally adapted to the bodily shape of the infant.

FIG. 8 illustrates an embodiment of a netting elastic according to the invention which is modified in relation to FIG. 4. A number of elastic threads 26 are located at the side edge portions of the diaper while extending with portions 26' right across the crotch portion of the diaper. These single elastic threads 26 are attached to inelastic threads 27 which are in turn affixed to the front end of the diaper.

FIG. 9 illustrates a rectangular diaper consisting of an absorption body 28 and outer layers 29 applied to both sides thereof and extending with edge portions 30, 31 laterally outside the absorption body. The network incorporated in this inventive diaper is formed of transverse elastic threads 32 and longitudinal elastic threads 33, said latter threads being disposed at the side portions 30 and 31 of the outer layers 29. The outer layers are united around the absorption body, and the network is connected with one of these outer layers. The transverse elastic threads are lying most closely spaced in the midportion of the diaper, and the mutual distance between them is continually increased in the direction towards the diaper ends. The figure illstrates the network in a stretched condition with equal tension in all threads. When relieved, the elastic netting will give the initially rectangular diaper a shape with a narrower crotch portion at its center, the bulk and thickness of the diaper thus being largest within this region.

The diaper shown in FIG. 10 consists of an absorption body 34 having a narrow, rounded center portion 35, and outer layers 36 on either side of the absorption body. The outer layers extend with portions 37, 38 laterally outside the absorption body while being provided with rounded cutouts at the diaper mid-section for creating a crotch portion with smaller dimension than the rest of the diaper. The outer layer portions extending outside the absorption body are interconnected to form a closure around the absorption body. According to the invention, an elastic network 39 is affixed to one of said outer layers in a prestretched condition. When applied, this network has been held only at the points denoted 40, the transverse elastic threads 41 in the netting thereby giving the longitudinal elastic threads 42 the arched curvature shown in FIG. 10.

FIG. 11 illustrates a sanitary napkin made in accordance with the invention and consisting of an absorption body 43 having outer layers 44 applied to both sides thereof, said layers surrounding the absorption body extending outside it and being united there. According to the invention, an elastic network 45 is applied to one of the outer layers. Said network is elastic longitudinally as well as transversely to the napkin while, a seen in FIGS. 12 and 13, having for its purpose to give the napkin a shape adapted to the body of the wearer, as well as elevating the outer layers extending outside the side edges of the absorption body for creating a border 44'. Preshaping the sanitary napkins is in fact an extremely important procedure to avoid uncontrolled deformation during use. By means of the inventive network comprising both longitudinal and transverse elastic, the elevation of the side borders can be controlled in order to make them rise in the appropriate direction.

FIGS. 14 and 15 illustrate schematically an absorption article according to a further embodiment of the invention. The distinguishing feature thereof is the very close meshing of its network 46 while being applied to the outer layer 47 intended for contact with the body of the wearer. Besides the purpose of forming longitudinal and transverse elastic for example, the network 46 is intended to give the outer layer a three-dimensional structure for increasing the volume of the article and to create an insulation layer between the wearer and the absorption body having become moist during use of the product. The material in the outer layer 47 serving as an insulating layer is therefore suitably a hydrophobic material. The structure of the insulation layer 47 is clearly shown in FIG. 15.

The network in an absorption article according to the invention is suitably made by knitting or crocheting and consists either of elastic threads alone, or of both elastic and inelastic threads.

FIG. 16 illustrates schematically a method of producing web portions 49 for single absorption articles from an inventive continuous knitted or crocheted network web 48. According to FIG. 16 said web is knitted or crocheted in a square-shaped pattern consisting of longitudinal and transverse elastic threads 50 and 51 being retained in a prestretched condition. The network web obtained is fed in the direction of the arrow A for application onto a layer of casing material web in a diaper manufacturing process, the single diapers thereby being manufactured while positioned with its longitudinal direction across the network web. Before applying the network web portions constituting the final network in a finished absorption article to the layer of material web, the network web is cut off at spaced intervals in its transverse direction for obtaining said separate web portions. This process is synchronized with the manufacture of individual diapers. After being severed, the network web remains unbroken only in the longitudinal direction along the edges, whereas the threads running across the web in each one of the accomplished web portions 49 are given an arch-shaped curvature, as shown in FIG. 16. Said web portions 49 are affixed to the layer of casing material web in this condition, thus forming an arch-shaped, almost hourglass-like elastic on the completed single diapers. Its curvature can be controlled partly by varying the thread tension in the network web and partly by the way of cutting the network web transversely.

Figure 17:
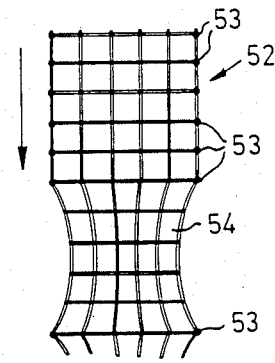

FIG. 17 illustrates how to obtain the inventive arch-shaped curvature on diapers being manufactured in a path with the longitudinal direction of the diapers oriented in the direction of manufacture. A network web 52 is knitted or crocheted continuously in this case as well. Said web is retained at prickles 53 along the edges of the web. For producing individual network web portions 54 with arch-shaped elastic, intended for single diapers, the network web is hooked off in a manner not further defined from some of the prickles prior to being applied to a casing material web or the like forming part of the diaper manufacturing process.

As already mentioned, the network in an inventive absorption article can be manufactured from elastic as well as inelastic threads. The network may further include threads of various elasticity.

Figure 18:
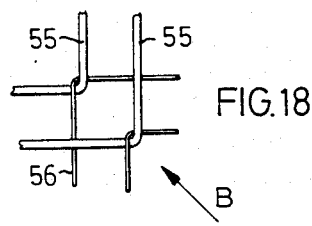

FIG. 18 finally illustrates purely schematically an example of how the inventive network may be knitted for providing elastic lines of action wherever required. Elastic threads 55 are hooked onto inelastic threads 56, the elastic line of action thereby being located in the direction of the arrow B. According to this principle, an elastic network according to the invention can be knitted or crocheted with elastic lines of action in the desired directions.

The present invention is not restricted to the embodiments illustrated and described above, since a plurality of modifications are conceivable within the scope of the claims. For example, the elastic network may incorpoate pre-meshed polymer threads being stretched in its plastic state prior to application in the network. By heating the elastic network in order to shrink the pre-meshed polymer threads included therein, the extension and orientation of individual threads in the network may be altered, for example to achieve an arch-shaped edge elastic in a network produced with initially straight edges.

A network according to the invention can be utilized for diapers providing in this way both leg and waistband elasticity.

In the embodiments described above with reference to the drawings relating to diapers provided with an elastic network, this network has been applied to any one of the casing material layers directly surrounding the absorption body. In an absorption article according to the invention, however, the network can be attached to an additional layer of material included in the article. This additional layer of material with associated network elastic is then affixed to the outside of the liquid impermeable layer of the article only with its edge portions. This will result in an elastic outer layer which is slidable over the main part of its surface in relation to other layers of material in the diaper, and will therefore have approximately the same function as a single elastic pant when applying the absorption article in question.

We claim:

1. Absorption article such as a diaper or a sanitary napkin, comprising a liquid permeable first outer layer and a preferably liquid impermeable second outer layer being applied to either side of an absorption body for enclosing it, as well as elastic members applied in a prestretched condition for causing the edge portions of the article to fit closely around the body of the wearer, characterized in that the elastic members are included in a network of interesting elastic members extending over the crotch portion of the article and so disposed as to give the article elasticity in more than one direction.

2. Article according to claim 1 with the two outer layers laterally extending outside the absorption body to achieve flexible side flaps intended to be closely fit to the body of the wearer during use, characterized in that the network comprises substantially longitudinal elastic ribbons or threads arranged in the side flaps on both sides of the absorption body, as well as transverse elastic ribbons or threads intersecting the longitudinal bands at least at the center of the article, or in the crotch region of the diaper.

3. Article according to claim 2, characterized in that the longitudinal and transverse elastic threads or ribbons are made to coact and are interconnected for this purpose by means of knitting, crocheting or the like.

4. Article according to claim 3, characterized in that the transverse elastic ribbons or threads have various lengths, are applied at irregular mutual spacings or under various degrees of pretension thereby imparting the substantially longitudinal threads of the network to conform to a curvature adapted to the bodily shape of the wearer.

5. Article according to claim 4 made in the form of a diaper, characterized in that the transverse elastic ribbons or threads are applied with such ununiform length and/or thread tension that the longitudinal ribbons or threads disposed at either side of the absorption body will be arched and come closest together in that region of the diaper, substantially the mid-portion thereof, which has the lowermost position during use, the mutual spacing therebetween increasing continually from the diaper center and towards the diaper ends.

6. Article according to claim 1 made in the form of a diaper with its outer layers running outside the side edges of the absorption body and extending laterally in the direction from the crotch portion towards the rear end of the diaper outside these side edges under gradual increase of the distance therefrom, obtaining in this manner gradually widened flaps on either side of the absorption body, characterized in that the network comprises substantially longitudinal elastic ribbons or threads which, at least from the crotch portion of the diaper and rearwards, are applied in a substantially V-shaped pattern the apex thereof being disposed in the mid-portion of the diaper front end, and that said ribbons or threads intersect the side edges of the absorption body substantially within the crotch area, the network also comprising transverse elastic ribbons or threads uniting the longitudinal ribbons or threads.

7. Article according to claim 1 made in the form of a diaper, characterized in that the network is elastic solely within the crotch area of the diaper, the remaining components constituting inelastic or non-stretched ribbons or threads.

8. Article according to claim 7, characterized in that the elastic zone of the network is at least partially hooked onto inelastic threads or the like.

9. Article according to, claim 1 characterized in that said elastic members comprised in the network are secured in deflection points by means of inelastic threads.

10. Article according to claim 1 characterized in that the network is applied to the liquid permeable outer layer, the liquid impermeable outer layer being stretched around the absorption body and pulled up towards the front of the article for providing a liquid-proof barrier layer around the side edges of the absorption body.

11. Article according to claim 1 characterized in that the network is formed of weldable ribbons or threads.

12. Article according to claim 1, characterized in that the network is affixed to the liquid impermeable layer, that elastic ribbons or threads are arranged under comparatively high tension to border a central region extending over the crotch area and widening from there both forwardly and rearwardly of the article, and that the heavily prestretched ribbons or threads, at least over the entire crotch area, are positioned over the absorption body and outside said central zone.

13. Article according to claim 1 characterized in that the network is very closely meshed and is applied to the outer layer facing the wearer during use, the network thereby imparting to the outer layer, in addition to a sealing and conforming elastic, a three-dimensional structure for creating an insulating layer between the wearer and the absorption body contained in the article.

14. Article according to claim 1 made in the form of a diaper, characterized by comprising an additional layer superimposed on the liquid impermeable layer and preferably made of a non-woven textile material, said additional layer at least over substantially the major portion of its area not being affixed to the liquid impermeable layer, and by the network being secured to said additional layer thereby making it slidable over the liquid impermeable layer on the inside thereof, serving in this manner substantially the same purpose as a separate baby pant.

15. Method in the continuous manufacture of an absorption article such as a diaper or a sanitary napkin for applying elastic members, whereby individual absorption cores are fed out on a production line while being enclosed between a web of liquid permeable material, preferably a non-woven textile material, and a liquid impermeable web of material, preferably a plastic film, said webs of material being united around each absorption core and then secured therebetween for obtaining single absorption articles, characterized in that a network containing intersecting elastic members is advanced while keeping pace with the webs of material and is affixed to at least one of these, or to a simultaneously fed additional web of material secured to the outside of the liquid impermeable web of material, the network thereafter being cut off together with the webs of material thereby producing single absorption articles provided with elastic.

16. Method according to claim 15, characterized in that the network is continually formed during manufacture of the absorption articles by means of knitting, crocheting or gluing.

17. Method according to claim 15 for the manufacture of absorption articles lying with their longitudinal extension oriented in the direction of feed on the assembly line, characterized in that the network (52) is maintained under tension across the production line while being stretched only at spaced points (53), the elastic members therein thus being caused to take the desired curvature prior to attaching the network to the web of material, said curvature being variable by altering the points of attachment in relation to the absorption cores.

18. Method according to claim 15 for the manufacture of absorption articles lying with their longitudinal extension across the direction of feed on the assembly line, characterized in that the network (48) fed synchronously with the other webs of material forming part of the manufacturing process is maintained under tension and is cut a distance across the web between the separate absorption bodies before being joined to any one of the other webs of material included in the manufacturing process, said network thereby being caused to take a curvature corresponding to that of the separate absorption articles.

19. Method according to claim 16, characterized in that the network is knitted or crocheted from elastic as well as inelastic threads thereby making it elastic within areas and/or along lines of action in accordance with the knitting or crochet pattern.

20. Method according to claim 15 in which the network comprises pre-meshed polymer threads having been stretched out in its plastic state before being attached to the network, characterized in that the network, before or after attachment to the absorption articles, are heated in order to shrink said threads, the orientation of the other threads contained in the network thereby being altered.

21. Method according to claim 20, characterized in that the threads which are shrinkable by the supply of heat are applied to the network at spaced points transversely thereto, and that the orientation of elastic threads initially stretched in the longitudinal direction of the network is altered by heating said network.

22. Method according to claim 20 in the manufacture of diapers with leg elastic, characterized in that the threads being shrinkable by heating are applied along those portions of the network intended to serve as leg elastic, and that the prestretched condition thereof is obtained by shrinking said threads with the aid of heat.

23. Method according to claim 20 in the manufacture of diapers with waistband elastic, characterized in that the threads being shrinkable by heating are applied along those portions of the network intended to serve as waistband elastic, and that the pre-stretched condition thereof is obtained by shrinking said threads with the aid of heat.

24. Absorption article according to claim 1 which said network also comprises inelastic members.

* * * * *